United States Patent [19]

Yoshitomi et al.

[11] Patent Number: 4,990,779
[45] Date of Patent: Feb. 5, 1991

[54] METHOD AND APPARATUS FOR EVALUATING STRAINS IN CRYSTALS

[75] Inventors: Yasunari Yoshitomi, Kitakyushu; Kuniteru Ohta, Sagamihaia; Shuichi Funaki, Nakahara, all of Japan

[73] Assignee: Nippon Steel Corporation, Tokyo, Japan

[21] Appl. No.: 361,925

[22] Filed: Jun. 6, 1989

[51] Int. Cl.⁵ .................................... G01N 23/203
[52] U.S. Cl. ................................. 250/310; 250/306; 250/307
[58] Field of Search ............... 250/310, 311, 307, 306; 73/763, 774, 78

[56] References Cited

U.S. PATENT DOCUMENTS

| | | | |
|---|---|---|---|
| 3,702,398 | 11/1972 | Van Essen et al. | 250/310 |
| 3,861,199 | 1/1975 | Barkhoudarian | 250/310 |
| 3,866,044 | 2/1975 | Grund | 250/310 |
| 4,006,357 | 2/1977 | Kanda et al. | 250/310 |
| 4,146,788 | 3/1979 | Mirkin et al. | 250/310 |
| 4,160,162 | 7/1979 | Müller et al. | 250/311 |
| 4,253,154 | 2/1981 | Russ et al. | 250/310 |

OTHER PUBLICATIONS

Kikuchi-like Reflection Patterns obtained with the Scanning Electron Microscope, D. G. Coates, pp. 1179-1184.

Contrast Mechanisms of Special Interest In Materials Science, D. E. Newbury and H. Yakowitz, pp. 149-211.

Deformation Studies At Sliding Wear Tracks In Iron, A. W. Ruff, pp. 59-75.

Primary Examiner—Jack I. Berman
Assistant Examiner—Kiet T. Nguyen
Attorney, Agent, or Firm—Kenyon & Kenyon

[57] ABSTRACT

The strains in crystals are evaluated by quantifying the sharpness of an electron channeling pattern and determining changes in the quantified sharpness of the electron channeling pattern. There is such a close correlation between the sharpness of the electron channeling pattern and the strains in crystals that the latter can be evaluated in terms of changes in the former. An apparatus for evaluating strains in crystals comprises a scanning electron microscope having a function to form an electron channeling pattern and an image analyzer having a function to quantify the sharpness of an electron channeling pattern.

8 Claims, 4 Drawing Sheets

METHOD AND APPARATUS FOR EVALUATING STRAINS IN CRYSTALS

BACKGROUND OF THE INVENTION

1. Field of the Invention

This invention relates to a method and apparatus for evaluating the strain in steel, silicon and other crystalline substances.

2. Description of the Prior Art

The strain in steel and other crystalline substances has conventionally been evaluated commonly by determining the spreading of diffracted beams of X-rays passed therethrough or determining their Vickers hardness.

But X-ray diffraction analysis is unfit for the evaluation of strain in a very small area because beams of X-rays are difficult to focus to such a small area as under 10 μm across. Another shortcoming is low sensitivity of the spreading of diffracted X-ray beam to the strain. Evaluation by Vickers hardness, on the other hand, takes advantage of a phenomenon that the hardness of a material varies with its dislocation density (or strain). But this method also does not provide very accurate evaluation because solid solutions and precipitates in crystals also affect the hardness of the material being examined.

Electron Channeling Pattern (hereinafter abbreviated ECP) is a phenomenon discovered by D. G. Coates (D. G. Coates: Phil. Mag., 16 (1967), p. 1179). When electron beams are irradiated on a specimen of crystalline substance not too thin, part of the electrons having entered the specimen is elastically scattered while maintaining the incident energy because of the interaction with the constituent atoms of the crystal, with the rest being inelastically scattered losing the incident energy. Part of the incidence energy lost is used for the excitation of the electrons in the atoms making up the crystalline substance. Of the excited electrons, those emitted from the surface of the specimen are called secondary electrons. Of the inelastically scattered electrons, those emitted from the surface of the specimen are called back-scattered electrons. When the surface of the specimen is scanned with electron beams irradiated at varying angles, the intensity of the secondary and back-scattered electrons changes greatly because of the diffraction at the crystal plane in the vicinity of the Bragg angle $\theta_B$ at which the incident angle $\theta$ of the electron beams with respect to the crystal plane satisfies Bragg's law $n\lambda = 2d \sin \theta$, wherein n is the order of reflection, $\lambda$ the wavelength of electron beams, and d the interval between crystal planes. On detecting the intensity of the secondary or back-scattered electrons and inputting the signal representing the detected intensity to a CRT display or other recording device synchronously with the scanning signal of the electron beams, an image with varying light and shade appears at and near the Bragg angle $\theta_B$. Scanning electron microscopes are widely used to obtain ECP's.

The ECP is known to provide information about the orientation and perfectness of crystals. Regarding the perfectness of crystals, it is known that the ECP blurs when crystals are strained (D. E. Newbury and H. Yakowitz: Practical Scanning Electron Microscopy, ed, by J. I. Goldstein and H. Yakowitz (1975), p. 149 [Plenum Press]). But the intricateness of the ECP and other factors have so far hampered the quantitative evaluation of strains. Though it is known that strains can be quantified using the contrast of specific pseudo-Kikuchi lines in the ECP as a parameter (Wear, 1976, 40, p. 59), this method is inapplicable to the quantification of strains in an arbitrarily chosen crystal orientation.

Evaluation of the nonuniform distribution of work-induced strain, the amount of strain accumulated in different crystal orientations and the residual strain resulting from softening is extremely important for the development of recrystallization and texture control technologies. As such, there is a pressing need for the development of a reliable micro-strain evaluation method based on the conventionally established principles.

Noting a phenomenon that the ECP suddenly blurs when a micro-strain is applied on crystals, the inventors made an extensive analysis of ECP's using an image analyzer. The analysis led to a new discovery that image analysis of the ECP is very effective for the evaluation of the microstrain in such crystalline substances as steel.

SUMMARY OF THE INVENTION

The object of this invention is to provide a method and apparatus for evaluating crystal strains that overcome the conventional difficulty in the quantitative evaluation of micro-strains in crystals.

A method of evaluating crystal strains according to this invention comprises quantifying the sharpness of the ECP and determining the magnitude of crystal strain from a change in the quantified sharpness of the ECP. Here, the sharpness of the ECP means the contrast between the dark and bright areas in an overall image of the ECP quantified. Because of the close correlation between them, crystal strain can be evaluated by determining the sharpness of the ECP.

The ECP can be obtained by use of, for example, a scanning electron microscope having an ECP forming function.

The sharpness of the ECP can be quantified by several methods. One of them differentiates (by unidirectional differentiation, Sobel method, etc.) the light and shade across the ECP with respect to length (or distance) using an image analyzer and determines the ratio of an area showing higher derivatives to the entire area of the ECP. Another method uses the highest derivative as the criterion of sharpness. Still another method uses the difference between the brightest and darkest portions of the ECP as the criterion of sharpness. This invention can quantify the sharpness of the ECP by any of these conventional methods.

The crystal strain may also be evaluated by determining the ratio of an area in which the light and shade varies greatly to the entire area of the ECP. The ECP is an extremely complex image in which waves diffracted by all planes of crystals are shown at a time, with a strain blurring individual diffracted waves differently. Thus, it is effective to determine the ratio of an area in which the light and shade changes beyond a given threshold limit and evaluate the average sharpness of the diffracted waves appeared. The higher the threshold limit, the smaller will be the chosen area (a sharp portion of the ECP). On the other hand, more noise will be involved if the threshold limit is lowered. Therefore, a threshold limit that permits a large enough sharp area to be chosen while keeping the noise level at a satisfactorily low level should be determined experimentally. The threshold limit must of course be chosen from within a proper range. A threshold limit chosen from within a proper range assures an accurate relative evaluation of strains. If the best-suited threshold limit is chosen for each individual application, the accuracy of crystal strain evaluation will be increased. Changes in the light and shade may be determined by any of the conventional methods such as unidirectional differentiation and the Sobel method with an image analyzer.

A crystal strain evaluation apparatus of this invention comprises a scanning electron microscope with an ECP forming function and an image analyzer having a function to quantify the sharpness of an ECP. Any type of image analyzer may be used so far as it has the required ECP sharpness quantifying function. ECP images produced by a scanning electron microscope may be input into an image analyzer either by directly sending electric signals representing an ECP image from the scanning electron microscope to the image analyzer or inputting into the image analyzer image signals made by a television camera that picks up an image produced by the scanning electron microscope (either as an image on a CRT display or in the form of a photograph thereof).

The method and apparatus of this invention permit evaluating micro-strains in crystals by quantifying the sharpness of ECP's. This feature permits accurate evaluation of residual strains in hot-rolled steel plates and those resulting from the softening processes (recovery and recrystallization). The ECP provides information about the perfectness of crystals in a surface region of not more than 500 Å in depth and approximately 3 μm across. Therefore, it can be used in the investigation and analysis of nonuniform deformation in working, difference in accumulated strains due to the crystal orientation and the nucleation site of recrystallization. As the strain can be construed as representing the amount of lattice defects, this invention is also applicable to the investigation of defects in semiconductors etc. ascribable to lattice defects and to the detection of strains in silicon and other semiconductor materials.

DESCRIPTION OF THE PREFERRED EMBODIMENTS

Figure 1:
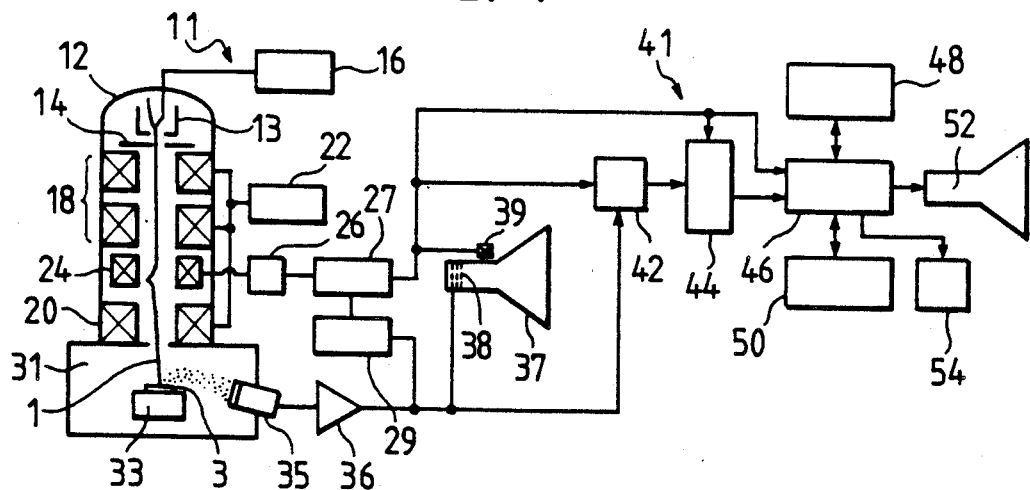
FIG. 1 is a block diagram of a crystal strain evaluating apparatus according to this invention.

FIG. 1 shows a crystal strain evaluating apparatus of this invention.

The crystal strain evaluating apparatus comprises a scanning electron microscope 11 and an image analyzer 41. The scanning electron microscope 11 is an ordinary electron microscope having an ECP forming function. At the top of a microscope tube 12 is provided an electron gun 13 connected to an acceleration high-voltage power supply 16. A focusing lens 18 is provided directly under the anode of the electron gun 13, with an objective lens 20 at the bottom of the tube 12. The focusing lens 18 and objective lens 20 are connected to a lens power supply 22. The focusing lens controls the amount and spot size of electrons reaching a specimen 3. The objective lens 20 performs image focusing. Between the focusing lens 18 and objective lens 20 is disposed a deflecting coil 24. To the deflecting coil 24 is connected a scanning signal generator 27 through a multiplier 26. Comprising an X-and Y-direction scanning coils, the deflecting coil 24 deflects the electron beams 1 on signals from the scanning signal generator 27, thus two-dimensionally moving the incident angle of the electron beams 1 reaching the surface 4 of the specimen. A blanking circuit 29 is connected to the scanning signal generator 27. The lower end of the tube 12 communicates with a specimen chamber 31. A specimen stand 33 is provided in the specimen chamber 31, with a detector 35 disposed to face the specimen stand 33. The detector 35 detects the amount or intensity of secondary electrons emitted from the surface 4 of the specimen on irradiation of electron beams 1 and convert the intensity into an electrical signal. For detecting back-scattered electrons, the detector is disposed around a hole through which electron beams are sent into the specimen chamber 31. The detector 35 is connected to a CRT display 37 through an amplifier 36. The blanking circuit 29 is connected to the electron gun 38 of the CRT display 37 and the scanning signal generator 27 is connected to a deflecting coil 39. The signals resulting from the detection by the detector 35 are fed into the CRT display 37 in synchronism with the scanning of the surface 4 of the specimen by the electron beams 1.

The image analyzer 41 comprises an A-D (analog-to-digital) converter 42 to convert the analog signals from the detector 35 of the scanning electron microscope 11 into digital signals and a central processing unit 46 connected to the A-D converter 42 through an image memory 44. To the central processing unit 46 is connected a main memory 48, an image processor 50, a CRT display 52 and a printer 54. The scanning signal generator 27 of the scanning electron microscope 11 is connected to the A-D converter 42, image memory 44 and central processing unit 46. The image memory 44 serves as a buffer when feeding the image signal from the A-D converter 42 into the main memory 48. The image processor 50 performs noise elimination, edge detection and other image processing.

The following paragraphs describe how the apparatus just described analyzes the strain in crystals.

Figure 2:
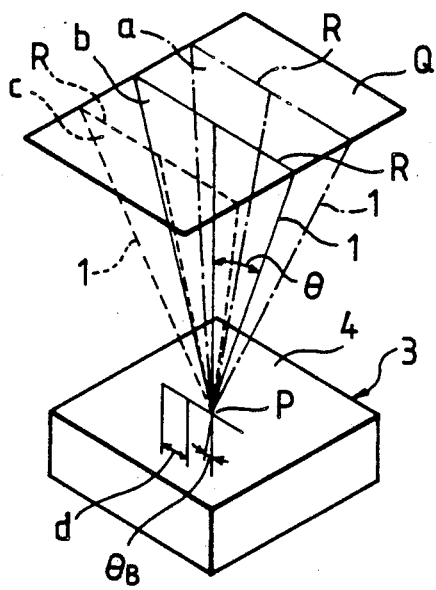
FIG. 2 illustrates how the surface of a specimen of a crystalline substance is scanned with electron beams.
Figure 3A:
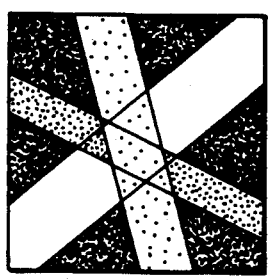
FIG. 3a is a schematic illustration of an ECP and FIG. 3b is a schematic illustration of a binary ECP.

As schematically shown in FIG. 2, the surface 4 of a specimen 3 of a crystalline substance is two-dimensionally scanned with electron beams 1 directed to a fixed point of impact P, with the angle of incidence θ rocked. While doing angular scanning by varying the incidence angle θ of the electron beams 1 in plane a, the detector detects secondary or back-scattered electrons. When the angular scanning in plane a is over, the same process is repeated in planes b, c and so on. The straight lines R in imaginary scanning plane Q correspond to the scanning angles in individual planes a, b, c and so on. Scanning is performed so that the incidence angle $\theta$ of the electron beams 1 with respect to the surface 4 of the specimen ranges from an angle smaller than Bragg angle $\theta_B$ to a larger one. The intensity of the secondary or back-scattered electrons detected by the detector is converted into an electric signal which is fed into the CRT display 37 in synchronism with the scanning signal of the electron beams 1. The intensity of the secondary or back-scattered electrons varies greatly within a narrow angular range on both sides of the Bragg angle $\theta_B$. When the signal is reproduced on the CRT display 37, therefore, a pattern of bands and lines appear thereon. FIG. 3a schematically shows an ECP reproduced on the CRT display 37. For simplicity, linear patterns are omitted in FIG. 3a. The ECP is made up of several differently oriented bands because the electron beams having entered crystals are reflected on many crystal planes whose orientations are different from the angle of incidence.

Figure 3B:
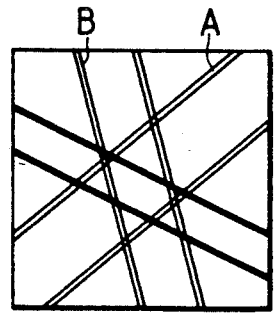

Meanwhile, the A-D converter 42 converts the signals from the detector 35 into digital signals that are then sent to the main memory 48 through the image memory 44. An instruction from the central processing unit 46 calls out an image data from the main memory 48 to the image processor 50 where image processing is carried out according to a flow chart in FIG. 4. First, noise elimination, linear conversion, contrast accentuation and other gray image processing are performed. The gray levels in linear conversion ranges from 0 to 255. Following this gray image processing, the light and shade of the image is differentiated in the direction of scanning. FIG. 3b schematically shows an image formed by outputting the absolute value of the derivative. The light and shade of the pattern varies greatly near the edge of the bands shown in FIG. 3a (because the intensity of the secondary or back-scattered electrons varies greatly within a narrow angular range on both sides of the Bragg angle $\theta_B$). Therefore, paired parallel bright lines appear along the edges of each band. After making another gray image processing, segmentation is carried out. After eliminating isolated points and applying other necessary processing, the extraction width of each line on the binary image is made equal. Then the ratio of the area of the bright lines to the entire area of the ECP is determined, which is then used as the criterion for the evaluation of crystal strains. Assume, for example, that lines A and B in FIG. 3b are chosen as the bright portions as a result of segmentation. After the width of both lines is made equal, the sum of the product of the length of line A multiplied by its width and the product of the length of line B multiplied by its width is divided by the whole area of the ECP to determine the parameter for evaluating crystal strains. The parameter thus determined is output by the printer 54. The light and shade of an ECP corresponds to the intensity of the secondary or back-scattered electrons detected by the scanning electron microscope 11, the brightness of the ECP reproduced on the CRT display 37 or the light and shade on a photograph of the ECP. Anyway, the image analyzer 41 processes the light and shade or sharpness of an ECP as electric signals.

Figure 4:
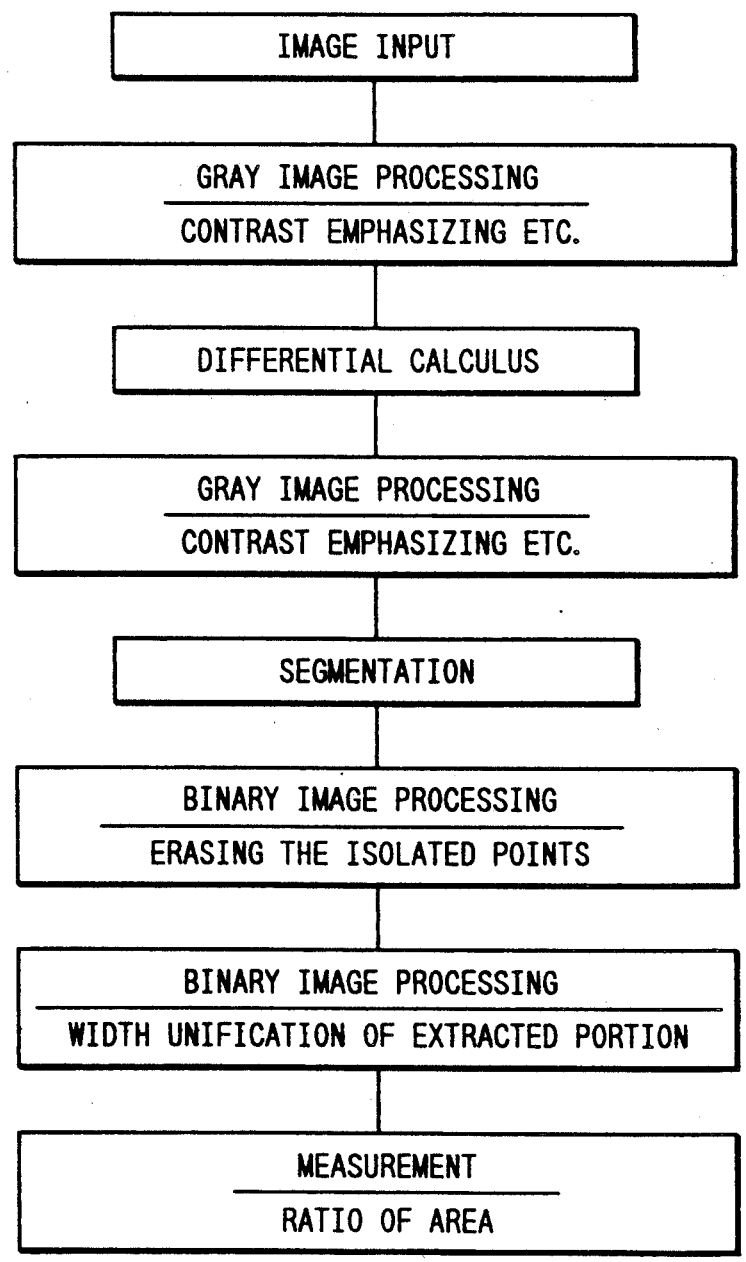
FIG. 4 is a flow chart of ECP image analysis.

The mechanism by which crystal strains can be evaluated through the quantification of the sharpness of an ECP is not definitely clear. But the inventors' interpretation is as follows: The lines on an ECP represent the beams diffracted from various crystal planes. When crystals deform, therefore, the diffracted lines blur, reducing the sharp contrast between the light and shade on the ECP. Presumably, therefore, the strain in crystals can be evaluated by determining the area ratio of a portion in which the sharpness exceeds a given threshold limit. Now the results of some experiments conducted on the basis of this invention will be described in the following:

The experiments were conducted by making image analysis according to the flow chart shown in FIG. 4 using a crystal strain evaluating apparatus comprising a scanning electron microscope (JSM-840) and an image analyzer (TOSPIX-II).

EXPERIMENT I

Figure 5:
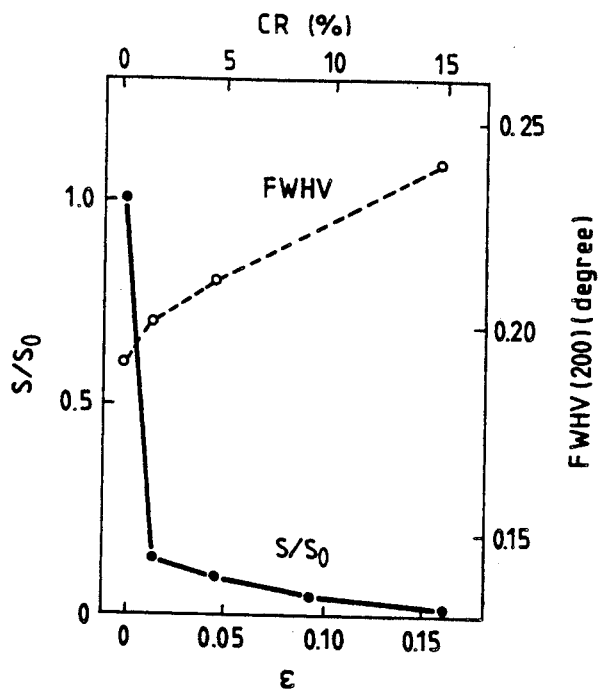
FIG. 5 graphically shows the relationship among the true strain in cold rolling, cold reduction ratio, sharpness of the ECP and the half-value width of the (200) diffracted X-rays.

FIG. 5 shows the relationship among the true strain in cold rolling ($\epsilon$), cold reduction ratio (CR), sharpness of an ECP ($S/S_0$) and half-value width of the (200) diffracted X-rays (FWHV). In this experiment, 0.340 mm thick annealed steel sheets containing 3.25% of silicon (with crystal grain size ranging from 10 $\mu$m to 50 $\mu$m) were cold-rolled. Changes in the sharpness of ECP's resulting from cold rolling were quantified with the image analyzer. The acceleration voltage of the electron beams was 35 KeV, irradiation current $6\times10^{-9}$ A, magnification 50, operating distance 8 mm and rocking angle $\pm8°$.

Measurement was made at the center of the thickness of each sheet. The points plotted in FIG. 5 are the averages of the measurements made at fifty each points (i.e., five points in the direction of cold rolling times ten points in the direction perpendicular thereto, the individual points being spaced at intervals of 1 mm). S represents the ratio of an area in which the light and shade of an ECP varies greatly, whereas $S_0$ denotes the value of S under an unstrained condition. As is obvious from FIG. 5, the sharpness of an ECP ($S/S_0$) is so sensitive to the presence of micro-strains that it can evaluate microstrains more effecitively than the conventional methods (such as the measurement of the half-value width of diffracted beams). An experimental strain-ECP sharpness ($S/S_0$) curve as shown in FIG. 5 must be prepared in advance. Then, the magnitude of the strain in a specimen under analysis can be determined by comparing the measured ratio $S/S_0$ of the specimen with that reference curve.

EXPERIMENT II

Annealed steel sheets having a thickness of 0.340 mm and containing 3.25% silicon were cold rolled with a cold reduction ratio of 0 to 15 percent. With each specimen thus prepared, the ratio of an area (S) in which the light and shade varies greatly to the whole area of the ECP was determined as shown in a histogram in FIG. 6. The ECP measurement was made at fifty points (five points in the direction of cold rolling times the points in the direction perpendicular thereto, the individual points being spaced at intervals of 1 mm) at the center of the thickness of each sheet. $\epsilon$ is the true strain. The acceleration voltage of the electron beams was 35 KeV, irradiation current $6\times10^{-9}$ A, magnification 50, operating distance 8 mm and rocking angle $\pm8°$.

Figure 6:
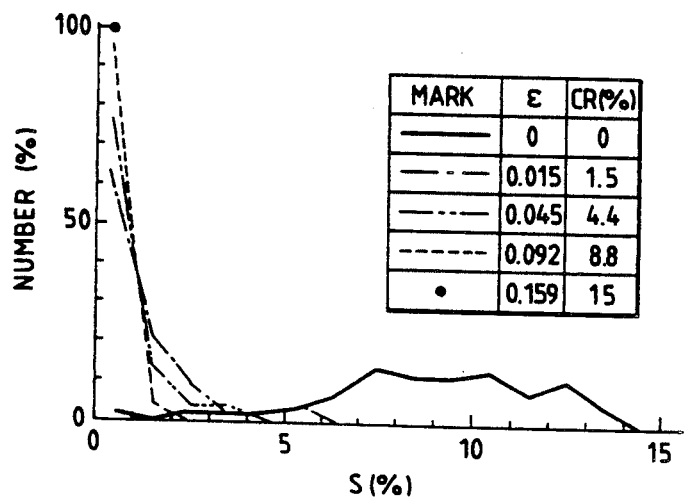
FIG. 6 is a histogram of the area ratio of a portion of annealed silicon steel plates in which the light and shade of the ECP varies greatly.

FIG. 6 shows that internal strains developed in the specimens as a result of cold rolling.

EXPERIMENT III

Hot-rolled silicon steel plates, 2.3 mm in thickness, containing 0.054% of carbon and 3.23% of silicon were treated under the following three different conditions:

(1) Held at 1150° C. for 30 seconds, slowly cooled to 900° C. in 2 minutes, and then air-cooled; (2) Held at 900° C. for 4 minutes and then air-cooled; and (3) Without annealing. With each specimen thus prepared, ECP measurement was made (a) at the center of the thickness of the plate and (b) at a depth ¼ of the thickness away from the surface of the plate. The ratio of the area S in which the light and shade varies greatly to the whole area of the ECP was determined as shown in a histogram in FIG. 7 (plotting the measurements at the center of the thickness) and FIG. 8 (plotting the measurements at ¼ of the thickness). The ECP measurement was made at fifty points (five points in the direction of cold rolling times ten points in the direction perpendicular thereto, the individual points being spaced at intervals of 1 mm; but ECP measurement was not made at a point where carbide was found and the number of measuring points in the direction of cold rolling was increased so that the total number always remains 50). The acceleration voltage of the electron beams was 35 KeV, irradiation current $6 \times 10^{-9}$ A, magnification 50, operating distance 8 mm and rocking angle ±8°.

Figure 7:
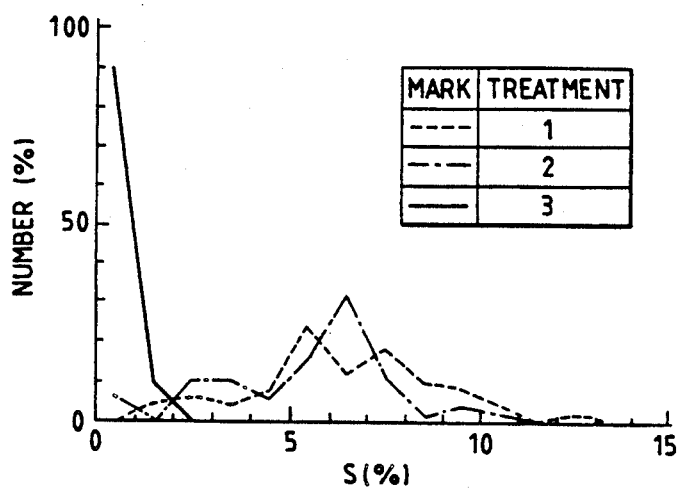
FIG. 7 is a histogram of the area ratio of a portion at the center of the thickness of silicon steel plates in which the light and shade of the ECP varies greatly.
Figure 8:
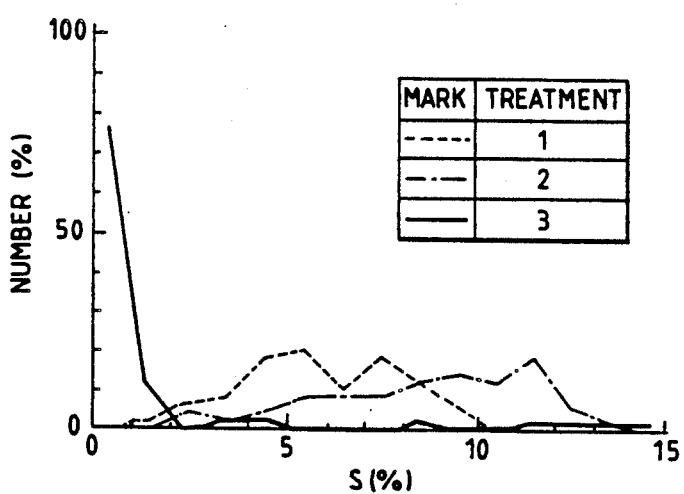
FIG. 8 is a histogram of the area ratio of a portion at ¼ of the thickness of silicon steel plates in which the light and shade of the ECP varies greatly.

As is obvious form FIGS. 7 and 8, work strains in the rolled steels decreased as a result of annealing.

EXPERIMENT IV

An ingot of silicon single crystal having a composition shown in Table 1 and growing in the <100> direction was sliced in the direction perpendicular to the direction of growth into 0.7 mm thick wafers.

The wafers were subjected to donor-killing annealing to eliminate oxygen at 650° C. for 20 minutes and reduced to have an ultimate thickness of 0.6 mm by mirror polishing the top surface and lapping the under surface. The mirror-finished surface was damaged by a sand-blasting applied under the conditions shown in Table 2. The acceleration voltage of the electron beans was 8 KeV, irradiation current $6 \times 10^{-9}$ A, magnification 50, operating distance 8 mm and rocking angle ±8°.

Figure 9:
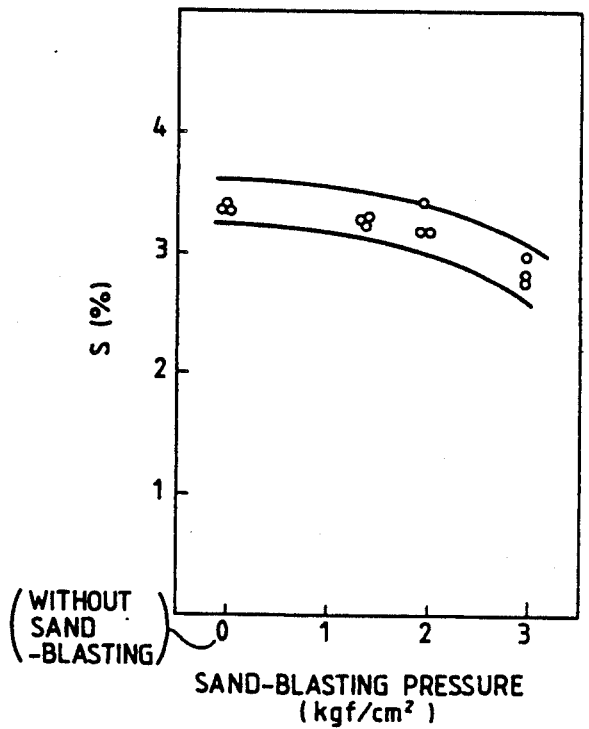
FIG. 9 is graphically shows the relationship between the sandblasting pressure and the area ratio of a portion in which the light and shade of the ECP varies greatly.

As is obvious from FIG. 9, the ratio of the area (S) in which the light and shade varies greatly to the whole area of the ECP corresponds to the intensity of the damage caused by sand-blasting, thus serving as a useful parameter in the evaluation of strains.

TABLE 1

| Oxygen Concentration | Carbon Concentration |
|---|---|
| $9.5 \times 10^{17}$ atoms/cm$^3$ | $1.5 \times 10^{17}$ atoms/cm$^3$ |

TABLE 2

| Specimen | Blasting Pressure (kgf/cm$^2$) | Particles Blasted |
|---|---|---|
| 1 | 0 | SiO$_2$ |
| 2 | 1.4 | 3.4~3.8 μm |
| 3 | 2.0 | in diameter |
| 4 | 3.0 | |

Involving all pseudo-Kikuchi lines, the method of this invention can be applied to the determination of strains in all crystallographic orientations. By contrast, the parameter employed by the conventional methods is the relative intensity of a pseudo-Kikuchi line corresponding to a specific crystal plane, such as, for example, the one in the (200) plane. Generally, not all pseudo-Kikuchi lines appear on a displayed ECP. The kind and number of pseudo-Kikuchi lines appearing vary with the crystallographic orientation of each measuring point. As such, the applicability of the conventional methods employing only specific pseudo-Kikuchi lines has been limited to certain crystallographic orientations.

This invention is by no means limited to the specific embodiments described. In feeding the signals representing an ECP into the image analyzer 41 in the apparatus shown in FIG. 1, for example, the pattern on the CRT display 37 of the scanning electron microscope 11 may be recorded on a video tape. The resulting signals are then fed into the A-D converter 42 of the image analyzer 41. In this case, the A-D converter 42, image memory 44 and control processing unit 46 are adapted to work in synchronism with the synchronizing signals from the videotape recorder. By the use of the SACP (selected area electron channeling pattern), crystal strains in as small an area as about 1 μm can be determined, too. An SACP can be obtained by, for example, bringing the cross-over point of the scanning electron beams 1 close to the surface of the specimen by turning off the lower one of the two deflecting coils one placed over the other.

The technology according to this invention evaluates the strains in crystals by quantifying the sharpness of the ECP. And technologies to quantify the sharpness of other similar improved patterns, such as the EBSP (electron back scattering pattern, J. A. Venables and C. J. Harland: Phil. Mag., 27 (1973), 1193), should be construed to come within the scope of this invention.

What is claimed is:

1. A method of evaluating the strains in crystals comprising the steps of:
   irradiating beams of electrons on the surface of a specimen of a crystalline substance, the surface of the specimen being scanned with the electron beams whose angle of incidence ranges from an angle smaller than the Bragg angle to a larger one;
   determining the intensity of secondary or back-scattered electrons discharged from the surface of the specimen;
   forming an electron channeling pattern containing several pseudo-Kikuchi lines by recording the intensity of the secondary or back-scattered electrons in synchronism with the scanning signals of the electron beams;
   determining the sharpness of the electron channeling pattern; and
   evaluating the strain in the crystalline substance on the basis of a change in the sharpness of the electron channeling pattern.

2. A method of evaluating the strains in crystals according to claim 1, in which said electron channeling pattern is formed by a scanning electron microscope having an electron channeling pattern forming function.

3. A method of evaluating the strains in crystals according to claim 1, in which the brightness of said electron channeling pattern throughout the entire area thereof is differentiated with respect to the length thereof, using the ratio of an area showing higher derivatives for determining sharpness.

4. A method of evaluating the strains in crystals according to claim 1, in which the brightness of said electron channeling pattern throughout the entire area thereof is differentiated with respect to the length thereof, using the ratio of an area showing the highest derivatives for determining sharpness.

5. A method of evaluating the strains in crystals according to claim 1, in which the difference between the brightest and darkest portions throughout the entire area of said electron channeling pattern is used for determining sharpness.

6. A method of evaluating the strains in crystals according to claim 1, in which the ratio of an area in which the light and shade varies greatly to the whole area of said electron channeling pattern is used for determining sharpness.

7. A method of evaluating the strains in crystals according to claim 1, in which the magnitude of strain is determined by comparing the actually determined sharpness of said electron channeling pattern with a preliminarily determined sharpness curve representing strains in crystals.

8. An apparatus for evaluating strains in crystals comprising:
 a scanning electron microscope forming an electron channeling pattern containing several pseudo-Kikuchi lines which comprises means for scanning the surface of a specimen with beams of electrons whose angle of incidence with respect to the crystal plane is varied from an angle smaller than the Bragg angle to a larger one, means for detecting secondary or back-scattered electrons and means for recording the intensity of secondary or back-scattered electrons in synchronism with the scanning signals of the electron beams;
 an image analyzer having means for quantifying the sharpness of said electron channeling pattern formed by the scanning electron microscope; and
 means for evaluating strain in the crystal based on change in the sharpness of said electron channeling pattern.

* * * * *